United States Patent
Liang et al.

(10) Patent No.: US 8,795,313 B2
(45) Date of Patent: Aug. 5, 2014

(54) DEVICE DETACHMENT SYSTEMS WITH INDICATORS

(75) Inventors: Jessica Liang, Irvine, CA (US); Dinh Nguyen, Garden Grove, CA (US); David Scott Beckham, Costa Mesa, CA (US); Christopher Charles Andrews, Lake Elsinore, CA (US)

(73) Assignee: Covidien LP, Mansfield, MA (US)

( * ) Notice: Subject to any disclaimer, the term of this patent is extended or adjusted under 35 U.S.C. 154(b) by 215 days.

(21) Appl. No.: 13/249,203

(22) Filed: Sep. 29, 2011

(65) Prior Publication Data

US 2013/0085520 A1    Apr. 4, 2013

(51) Int. Cl.
*A61M 29/00* (2006.01)

(52) U.S. Cl.
USPC ............................................... 606/195; 606/1

(58) Field of Classification Search
USPC .................................... 606/1, 191, 194, 195
See application file for complete search history.

(56) References Cited

U.S. PATENT DOCUMENTS

| | | |
|---|---|---|
| 5,109,867 A | 5/1992 | Twyford, Jr. |
| 5,217,484 A | 6/1993 | Marks |
| 5,250,071 A | 10/1993 | Palermo |
| 5,261,916 A | 11/1993 | Engelson |
| 5,263,964 A | 11/1993 | Purdy |
| 5,282,806 A | 2/1994 | Haber et al. |
| 5,304,195 A | 4/1994 | Twyford, Jr. et al. |
| 5,368,592 A | 11/1994 | Stern et al. |
| 5,417,708 A | 5/1995 | Hall |
| 5,480,382 A | 1/1996 | Hammerslag et al. |
| 5,490,859 A | 2/1996 | Mische |
| 5,499,985 A | 3/1996 | Hein et al. |
| 5,562,698 A | 10/1996 | Parker |
| 5,669,905 A | 9/1997 | Scheldrup |
| 5,728,129 A | 3/1998 | Summers |
| 5,800,455 A | 9/1998 | Palermo et al. |
| 5,895,391 A | 4/1999 | Farnholtz |
| 5,980,514 A | 11/1999 | Kupiecki et al. |
| 5,989,242 A | 11/1999 | Saadat |
| 6,004,338 A | 12/1999 | Ken et al. |
| 6,022,369 A | 2/2000 | Jacobsen |
| 6,039,744 A | 3/2000 | Forber |

(Continued)

FOREIGN PATENT DOCUMENTS

| | | |
|---|---|---|
| CN | 1668250 A | 9/2005 |
| DE | 19547617 | 9/1997 |

(Continued)

OTHER PUBLICATIONS

U.S. Appl. No. 13/249,223, filed Sep. 29, 2011.

*Primary Examiner* — Victor Nguyen
(74) *Attorney, Agent, or Firm* — Elizabeth A. O'Brien, Esq.

(57) ABSTRACT

A medical device detachment system receives an elongate delivery member, having a lumen, and an elongate core member. The system includes a housing, a user input mechanism for receiving a user input to effect detachment of a medical device, such as an embolic coil, from a distal end of the delivery member, and a grasping mechanism for grasping and moving a proximal end of the core member relative to a proximal end of the delivery member. The system also includes a first sensor detecting positioning of the proximal end of the core member within the housing, and a second sensor, detecting movement of the grasping mechanism. An indicator is connected to the first and second proximity sensors and provides feedback to a user.

24 Claims, 6 Drawing Sheets

(56) References Cited

U.S. PATENT DOCUMENTS

| | | | |
|---|---|---|---|
| 6,063,070 A | 5/2000 | Eder | |
| 6,136,015 A | 10/2000 | Kurz et al. | |
| 6,152,947 A | 11/2000 | Ambrisco et al. | |
| 6,190,373 B1 | 2/2001 | Palermo et al. | |
| 6,203,547 B1 | 3/2001 | Nguyen et al. | |
| 6,270,508 B1 * | 8/2001 | Klieman et al. | 606/147 |
| 6,375,668 B1 | 4/2002 | Gifford et al. | |
| 6,397,850 B1 | 6/2002 | Scheldrup | |
| 6,464,699 B1 | 10/2002 | Swanson | |
| 6,589,236 B2 | 7/2003 | Wheelock et al. | |
| 6,589,251 B2 | 7/2003 | Yee et al. | |
| 6,656,351 B2 | 12/2003 | Boyle | |
| 6,911,039 B2 | 6/2005 | Shiu et al. | |
| 6,953,473 B2 | 10/2005 | Porter | |
| 6,964,683 B2 | 11/2005 | Kowalsky et al. | |
| 6,994,689 B1 | 2/2006 | Zadno-Azizi et al. | |
| 7,022,133 B2 | 4/2006 | Yee et al. | |
| 7,208,003 B2 | 4/2007 | Davis et al. | |
| 7,226,460 B2 | 6/2007 | Gibson et al. | |
| 7,294,146 B2 | 11/2007 | Chew | |
| 7,331,973 B2 | 2/2008 | Gesswein et al. | |
| 7,344,558 B2 | 3/2008 | Lorenzo et al. | |
| 7,377,932 B2 | 5/2008 | Mitelberg et al. | |
| 7,419,501 B2 | 9/2008 | Chiu et al. | |
| 7,591,829 B2 | 9/2009 | Gibson et al. | |
| 7,691,124 B2 | 4/2010 | Balgobin | |
| 7,708,755 B2 | 5/2010 | Davis, III et al. | |
| 7,722,636 B2 | 5/2010 | Farnan | |
| 7,722,637 B2 | 5/2010 | Barry et al. | |
| 7,753,931 B2 | 7/2010 | Diaz et al. | |
| 7,780,693 B2 | 8/2010 | Brady et al. | |
| 7,811,305 B2 | 10/2010 | Balgobin et al. | |
| 7,901,444 B2 | 3/2011 | Slazas | |
| 7,918,872 B2 | 4/2011 | Mitelberg et al. | |
| 8,007,509 B2 | 8/2011 | Buiser et al. | |
| RE42,758 E | 9/2011 | Ken et al. | |
| 8,016,852 B2 | 9/2011 | Ho et al. | |
| 8,029,466 B2 | 10/2011 | Wilson et al. | |
| 8,034,073 B2 | 10/2011 | Davis, III et al. | |
| 8,100,918 B2 | 1/2012 | Gandhi et al. | |
| 8,133,252 B2 | 3/2012 | Davis et al. | |
| 8,142,456 B2 | 3/2012 | Rosqueta et al. | |
| 2001/0037141 A1 | 11/2001 | Yee et al. | |
| 2002/0010481 A1 | 1/2002 | Jayaraman | |
| 2002/0072712 A1 | 6/2002 | Nool et al. | |
| 2002/0116024 A1 | 8/2002 | Goldberg et al. | |
| 2003/0014073 A1 | 1/2003 | Bashiri et al. | |
| 2003/0171770 A1 | 9/2003 | Kusleika et al. | |
| 2003/0199966 A1 | 10/2003 | Shiu et al. | |
| 2004/0002731 A1 | 1/2004 | Aganon et al. | |
| 2004/0002733 A1 | 1/2004 | Teoh | |
| 2004/0034363 A1 | 2/2004 | Wilson et al. | |
| 2004/0106946 A1 | 6/2004 | Ferrera et al. | |
| 2004/0181256 A1 | 9/2004 | Glaser | |
| 2004/0243228 A1 | 12/2004 | Kowalsky et al. | |
| 2005/0021023 A1 | 1/2005 | Guglielmi | |
| 2006/0025792 A1 | 2/2006 | Gibson et al. | |
| 2006/0025801 A1 | 2/2006 | Lulo et al. | |
| 2006/0025802 A1 | 2/2006 | Sowers | |
| 2006/0036281 A1 | 2/2006 | Patterson et al. | |
| 2006/0079926 A1 | 4/2006 | Desai et al. | |
| 2006/0106417 A1 | 5/2006 | Tessmer et al. | |
| 2006/0116714 A1 | 6/2006 | Sepetka et al. | |
| 2006/0200047 A1 | 9/2006 | Galdonik et al. | |
| 2006/0271097 A1 | 11/2006 | Ramzipoor et al. | |
| 2006/0276823 A1 | 12/2006 | Mitelberg et al. | |
| 2006/0276824 A1 | 12/2006 | Mitelberg et al. | |
| 2006/0278680 A1 | 12/2006 | Viola et al. | |
| 2007/0083219 A1 | 4/2007 | Buiser et al. | |
| 2007/0173757 A1 | 7/2007 | Levine et al. | |
| 2007/0179520 A1 | 8/2007 | West | |
| 2007/0185524 A1 | 8/2007 | Diaz et al. | |
| 2007/0239193 A1 | 10/2007 | Simon et al. | |
| 2007/0239255 A1 | 10/2007 | Hines | |
| 2007/0267281 A1 | 11/2007 | Smith | |
| 2007/0270936 A1 | 11/2007 | Andreas et al. | |
| 2008/0045997 A1 | 2/2008 | Balgobin et al. | |
| 2008/0097462 A1 | 4/2008 | Mitelberg et al. | |
| 2008/0228215 A1 | 9/2008 | Strauss et al. | |
| 2008/0243106 A1 | 10/2008 | Coe et al. | |
| 2008/0255542 A1 | 10/2008 | Nimgaard et al. | |
| 2008/0300616 A1 | 12/2008 | Que et al. | |
| 2008/0306504 A1 | 12/2008 | Win et al. | |
| 2009/0012554 A1 * | 1/2009 | Makower et al. | 606/191 |
| 2009/0018653 A1 | 1/2009 | Bashiri | |
| 2009/0024154 A1 | 1/2009 | Williams | |
| 2009/0062812 A1 | 3/2009 | Fitz | |
| 2009/0088832 A1 | 4/2009 | Chew | |
| 2009/0138036 A1 | 5/2009 | Nardone | |
| 2009/0163780 A1 | 6/2009 | Tieu | |
| 2009/0163986 A1 | 6/2009 | Tieu | |
| 2009/0177261 A1 | 7/2009 | Teoh et al. | |
| 2009/0182268 A1 | 7/2009 | Thielen et al. | |
| 2009/0254169 A1 | 10/2009 | Spenser et al. | |
| 2009/0270877 A1 | 10/2009 | Johnson et al. | |
| 2009/0287291 A1 | 11/2009 | Becking et al. | |
| 2009/0312748 A1 | 12/2009 | Johnson et al. | |
| 2010/0004673 A1 | 1/2010 | Denison et al. | |
| 2010/0030200 A1 | 2/2010 | Strauss et al. | |
| 2010/0094395 A1 | 4/2010 | Kellett | |
| 2010/0174269 A1 | 7/2010 | Tompkins et al. | |
| 2010/0234872 A1 | 9/2010 | Guo | |
| 2010/0256666 A1 | 10/2010 | Chen | |
| 2010/0268204 A1 | 10/2010 | Tieu | |
| 2010/0268251 A1 | 10/2010 | Chen | |
| 2010/0268252 A1 | 10/2010 | Chen | |
| 2011/0022003 A1 | 1/2011 | Tekulve | |
| 2011/0046657 A1 | 2/2011 | Guo et al. | |
| 2011/0106098 A1 | 5/2011 | Williams | |
| 2011/0106128 A1 | 5/2011 | Chen | |
| 2011/0118772 A1 | 5/2011 | Chen | |
| 2011/0118776 A1 | 5/2011 | Chen | |
| 2011/0172700 A1 | 7/2011 | Bose et al. | |
| 2011/0202085 A1 | 8/2011 | Loganathan et al. | |
| 2011/0208227 A1 | 8/2011 | Becking | |
| 2011/0265943 A1 | 11/2011 | Rosqueta et al. | |
| 2011/0282380 A1 | 11/2011 | Davis et al. | |
| 2011/0301686 A1 | 12/2011 | Bowman et al. | |
| 2011/0313447 A1 | 12/2011 | Strauss | |
| 2012/0041470 A1 | 2/2012 | Shrivastava et al. | |
| 2012/0041472 A1 | 2/2012 | Tan et al. | |
| 2012/0046687 A1 | 2/2012 | Trommeter et al. | |
| 2012/0065720 A1 | 3/2012 | Strauss | |
| 2012/0226305 A1 | 9/2012 | Strauss | |
| 2012/0316598 A1 | 12/2012 | Becking et al. | |
| 2012/0330347 A1 | 12/2012 | Becking et al. | |
| 2013/0066360 A1 | 3/2013 | Becking et al. | |
| 2013/0085521 A1 | 4/2013 | Lim | |
| 2013/0085522 A1 | 4/2013 | Becking et al. | |
| 2013/0123830 A1 | 5/2013 | Becking et al. | |
| 2013/0138136 A1 | 5/2013 | Beckham | |
| 2013/0211495 A1 | 8/2013 | Halden | |

FOREIGN PATENT DOCUMENTS

| | | |
|---|---|---|
| EP | 717969 A2 | 6/1996 |
| EP | 829236 | 3/1998 |
| EP | 853 955 | 7/1998 |
| EP | 996372 | 5/2000 |
| EP | 1400208 A1 | 3/2004 |
| EP | 1487526 | 12/2004 |
| EP | 1738698 A2 | 1/2007 |
| EP | 832 607 | 4/2008 |
| JP | 09-149904 | 6/1997 |
| JP | 10-201766 | 8/1998 |
| JP | 2004/073874 A | 3/2004 |
| JP | 2004-267749 A | 9/2004 |
| JP | 2006-051349 A | 2/2006 |
| JP | 2009-533202 A | 9/2009 |
| WO | WO-92/21400 | 12/1992 |
| WO | WO-93/11719 | 6/1993 |

(56) References Cited

FOREIGN PATENT DOCUMENTS

| WO | WO-94/06502 A2 | 3/1994 |
| WO | WO-98/34546 | 8/1998 |
| WO | WO-98/58590 | 12/1998 |
| WO | WO-01/58382 | 8/2001 |
| WO | WO-02/054943 A2 | 7/2002 |
| WO | WO-2007/070797 A2 | 6/2007 |
| WO | WO-2007/121405 | 10/2007 |
| WO | WO-2008/085606 | 7/2008 |
| WO | WO-2008/112435 | 9/2008 |
| WO | WO-2010/009019 | 1/2010 |
| WO | WO-2010/117883 | 10/2010 |
| WO | WO-2010/123821 | 10/2010 |

* cited by examiner (PRIOR ART)

DEVICE DETACHMENT SYSTEMS WITH INDICATORS

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious health consequences such as a stroke if one should rupture in the brain. Additionally, a ruptured aneurysm can also result in death.

Figures 1, 2A:
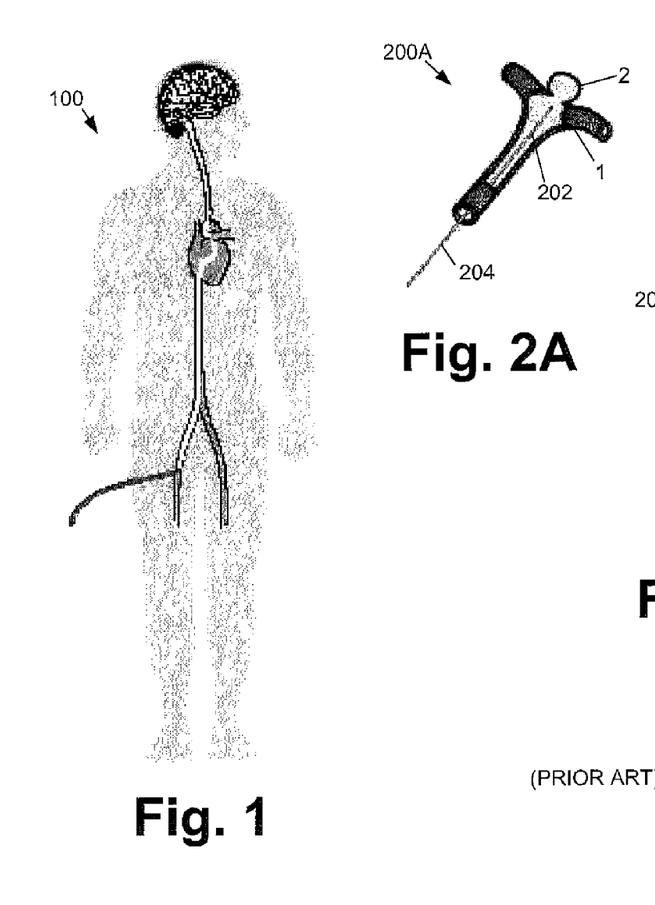
FIG. 1 depicts a cross section of a person showing certain vasculature and a catheter introduced into a femoral artery for introduction of an embolic coil for treating cerebral aneurysms according to the prior art.
FIGS. 2A-2C illustrate the introduction of an embolic coil into an aneurysm according to the prior art.

FIG. 1 depicts a cross section 100 of a person showing certain vasculature and a catheter introduced into a femoral artery for introduction of an embolic coil for treating cerebral aneurysms according to the prior art.

Figures 2B, 2C:
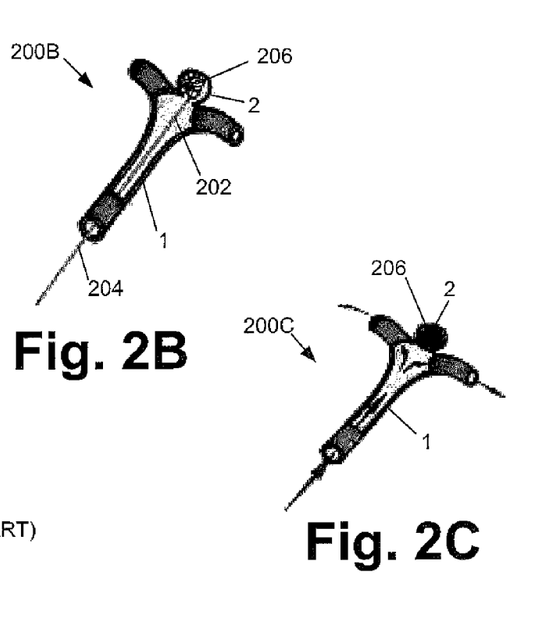

One approach in treating aneurysms utilizes an occlusive wire coil and delivery system for positioning the coil in a desirable site of a blood vessel. FIGS. 2A-2C illustrate cross sectional views 200A-200C of a portion of vasculature 1 showing the introduction of an embolic coil 202 into an aneurysm 2 by user of a pusher 204.

As shown in FIGS. 2A-2C, the embolic coil 202, once deployed, forms an occluding coil structure 206 within the aneurysm 2 (see FIGS. 2B-2C). One or more embolic coils 202 may be used to form coil structure 206. When the procedure is completed, the aneurysm 2 is effectively filled, allowing increased blood flow to downstream branches of the vasculature 1, as shown in FIG. 2C.

Such embolic coils have typically been placed at a desired site within the vasculature using a catheter and a pusher. As a first step, a flexible, small diameter catheter can be guided to the target site through the use of guidewires or by flow-directed means such as balloons placed at the distal end of the catheter. Once the target site has been reached, the catheter lumen is cleared by removing the guidewire (if a guidewire has been used), and the coil is placed into the proximal open end of the catheter and advanced through the catheter with a pusher. Pushers are essentially specialized wires having a distal end that is adapted to engage and push the coil through the catheter lumen as the pusher is advanced through the catheter. When the coil reaches the distal end of the catheter, it is discharged from the catheter by the pusher into the vascular site.

Several techniques have been developed to enable more accurate placement of coils within a vessel. In one technique, the coil is bonded via a metal-to-metal joint to the distal end of the pusher. The pusher and coil are made of dissimilar metals. The coil-carrying pusher is advanced through the catheter to the site, and a small electrical current is passed through the pusher-coil assembly. The current causes the joint between the pusher and the coil to be severed via electrolysis. The pusher can then be retracted leaving the detached coil at an exact position within the vessel. It is recognized that the electrolytic release of the coil requires a period of time for the metal-to-metal joint to dissolve, so that more rapid detachment of the coil from the pusher cannot occur.

Another wire coil and delivery assembly includes embolic coils that are attached to the connector of a probe assembly by a heat releasable adhesive bond. To release the embolic coil, laser energy is transmitted through the probe for heating the connector and adhesive bond. The laser apparatus required to produce laser energy, however, is a relatively expensive solution to manufacture and make available to clinicians.

Yet a further wire coil and delivery device comprise a platinum guidewire tip attached to a stainless steel guidewire. To release the platinum guidewire tip, a positive current is applied to the stainless steel guidewire for corroding away the guidewire in the bloodstream and releasing the platinum guidewire tip. This method of detaching the guidewire tip is relatively time intensive and may prolong the duration of an artificial embolization procedure.

SUMMARY

Described herein are embodiments of medical device delivery systems having a detachment system that detaches a medical device from the device delivery system and provides an indication that a condition has occurred sufficient to confirm detachment of the medical device from the device delivery system.

According to some embodiments, medical device detachment systems for placement of a medical implant in a patient's vasculature are described. In some embodiments, the systems include a housing configured to receive a proximal end of an elongate delivery member and a proximal end of an elongate core member slidably disposed within the delivery member; a grasping mechanism disposed within the housing and configured to grasp a portion of the core member in response to receiving an input signal; a user input mechanism configured to receive the input signal and permit movement of the grasping mechanism to grasp the proximal end of the core member; a first sensor configured to provide an output signal confirming placement of the proximal end of the core member at a determined position within the housing; a second sensor configured to provide an output signal indicative of a proximity of the grasping mechanism relative to the delivery member; and an indicator connected to the first and second proximity sensors and configured to receive one or more output signals from the first and second sensors and to provide corresponding indication signals to a user when one or more output signals are received from the first or second proximity sensors.

Some embodiments provide that the grasping mechanism is moveable from a first position within the housing to a second position within the housing, and wherein the second sensor is configured to detect when the grasping mechanism is at the second position. In some embodiments, the grasping mechanism comprises a pawl and anvil. In some embodiments, the user input mechanism comprises a slide.

In certain embodiments, the indicator comprises a light emitting diode (LED), and in some embodiments, the LED comprises a plurality of LEDs. Some embodiments provide that the indicator comprises two optical filters, each configured to pass a different wavelength band.

In some embodiments, the first sensor comprises a microswitch, which can comprise, in certain embodiments, a leaf-spring microswitch. In some embodiments, the second sensor comprises a microswitch, which can comprise a hinge microswitch. In some embodiments, the first sensor comprises a capacitive sensor. Some embodiments provide that the second sensor comprises a capacitive sensor. In some embodiments, the first sensor and/or the second sensor comprise a RF sensor. In some embodiments, the first sensor and/or second sensor comprise an acoustic sensor. In certain embodiments, the first sensor and/or second sensor comprise an optical detector.

In some embodiments, the indicator comprises a speaker, and in some embodiments, the indicator comprises a vibration generator. In certain embodiments, the indicator comprises a button disposed on the surface of the housing.

Some embodiments provide that the system further include a delivery member having a proximal end and a distal end, and an elongate core member disposed within the delivery member and having a proximal end and a distal end, and in some embodiments, the system further includes an embolic coil structure releasably attached to the distal end of the core member.

Some methods provided herein describe performing a medical device delivery procedure that include the following: to the vasculature of a patient, providing (i) an elongate delivery member having a proximal end and a distal end, (ii) an elongate core member disposed within the delivery member and having a proximal end and a distal end, and (iii) a medical device releasably connected to the distal end of the core member; providing the proximal end of the delivery member and the proximal end of the core member to a medical device detachment system that has indicators to indicate (i) a determined position of the proximal end of the core member within the system and (ii) a determined movement of the proximal end of the core member relative to the delivery member for detaching the medical device from the core member; seating the proximal end of the core member at the desired position within the medical device detachment system; indicating to a user the proximal end of the core member is at the determined position; with the medical device detachment system, moving the proximal end of the core member a determined distance relative to the proximal end of the delivery member to detach the medical device from the distal end of the core member; and indicating to a user the determined movement has occurred.

Some methods provide that moving the proximal end of the core member the determined distance relative to the proximal end of the delivery member comprises grasping the proximal end of the core member with a grasping device and drawing the proximal end of the core member proximally within the medical device detachment system. In some methods, moving the proximal end of the core member the determined distance relative to the proximal end of the delivery member comprises moving, in response to a user input, a slide connected to the grasping device. In certain methods, indicating to a user the core member is at the determined position comprises generating light from a light emitting diode connected to a sensor adjacent to the grasping device. In some instances, indicating to a user the determined movement has occurred comprises generating light from a light emitting diode connected to a sensor adjacent a position of the slide relative to a feed cone within the medical device detachment system.

In some methods further include placing the medical device at a determined location in the vasculature of a patient. In some methods, the determined distance is a distance sufficient to effect detachment of the medical device from the distal end of the core member. In certain methods, the medical device comprises an embolic coil.

These as well as other components, steps, features, benefits, and advantages of the present disclosure, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or similar components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

A medical device detachment system for placing/inserting/implanting a medical device at a desired location in a patient's vasculature by use of a pusher catheter and a housing with feedback indicators such as colored light emitting diodes. The pusher catheter can be an elongate delivery member with a lumen and an elongate core member. The indicators can indicate proper seating of a proximal end of the core member within the housing and detachment of the medical device from a distal end of the core member and/or delivery member.

The medical device detachment system includes a user input mechanism for receiving an input signal from a user, for initiating release of the medical device, and a grasping mechanism for holding and displacing a proximal end of the core member relative to a proximal end of an elongate delivery member disposed about the core member.

In the following description, exemplary embodiments of medical device detachment systems are referenced as coil detachment systems; the scope of the present disclosure, however, is not limited to use with coils, and any other medical devices that may be positioned in a patient, including other vasculature or other luminal body structure, by systems and/or methods according to the present disclosure. Although embodiments described herein discuss principles of the present disclosure in connection with one or more of these specific applications, these specific applications are provided to illustrate the general principles of the disclosure that can be used with other applications, devices, and procedures. Examples of medical devices that can be implanted include, but are not limited to, embolic coils, stents, and the like.

Figure 3A:
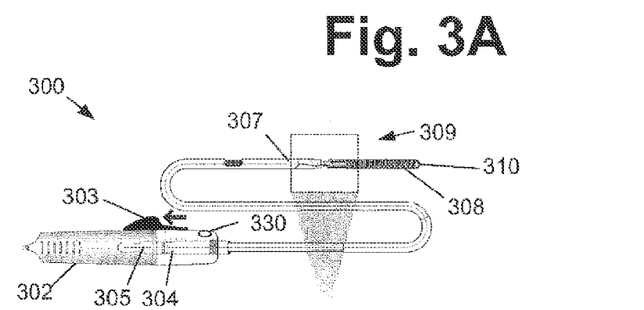
FIGS. 3A-3C illustrate an embodiment of a coil detachment system utilized with an elongate core member and embolic coil, including close up views of attached (B) and detached (C) states for the coil.
Figure 3B:
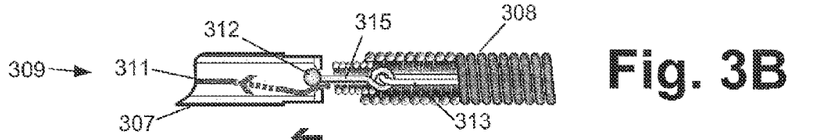
Figure 3C:
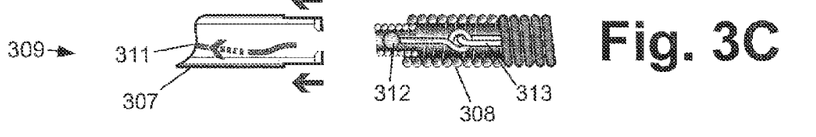

FIGS. 3A-3C depict an example of a coil detachment system 300 with an indicator 330, according to the present disclosure. FIG. 3A shows a partial cross section of the coil detachment system 300 having a housing 302 that receives proximal ends of an elongate delivery member 304, having a lumen and which also can be referred to as pusher or pusher tube, and an elongate core member 305, the distal ends of which are connected to an embolic coil 308. Close up views of the distal ends of the delivery member 304 and core member 305 are shown in FIG. 3B and FIG. 3C, showing attached and detached states for the embolic coil 308, respectively.

The coil detachment system 300 is configured to receive the delivery member 304 and core member 305 at proximal ends of both relative to the coil detachment system 300, with the coil 308 located at the distal ends of each. The coil detachment system 300 includes a user-input mechanism 303 that receives an input signal from a user and relays the input signal to a grasping mechanism (e.g., grasping mechanism 509 of FIG. 5) of the coil detachment system 300. The user input mechanism 303 functions to allow the user to cause detachment of the coil 308 at the distal end of the core member 305 by triggering the grasping mechanism (not shown) to displace the proximal end of the core member 305 relative to the proximal end of the delivery member 304. As shown in FIGS. 3A-3C, the coil detachment system 300 can form a larger system with the delivery member 304 and core member 305, which all together can form a still larger system with the embolic coil 308 and/or other medical device.

Regarding the user input mechanism 303, any suitable mechanism may be used that allows a user-supplied input signal to initiate the displacement of the proximal end of the core member 305 relative to the proximal end of the delivery member 304 to effect detachment of the embolic coil 308. In this way, a user such as a surgeon can cause detachment of the coil 308 at a desired time such as when the coil has been placed at a desired location within a patient's vasculature to treat an aneurysm. While exemplary embodiments described herein include a thumb slide as a useful user input mechanism 303, the scope of the present disclosure is not limited to such, and other types and/or forms of user input mechanisms may be used. Examples include, but are not limited to, mechanical switches, electromechanical switches, magnetic switches, electromagnetic switches, and/or combinations of such. User input mechanisms 303 may produce any type of suitable signals to initiate displacement of the proximal end of the core member 305 relative to the proximal end of the delivery member 304; such signals may be mechanical, electrical, magnetic, optical, RF, or any other type of signal and may be analog or digital. The user input signal can be initiated by any suitable user input modality, e.g., a button, a capacitive touch sensor, a keyboard, a moveable slide, and the like.

As indicated in FIG. 3B, embolic coil 308 is releasably held to the distal end of the core member 307 and the distal end of the delivery member 307. Such a releasable connection may be achieved, as shown, by a ball end 312 at the end of a link 315, which is configured within the coil 308 and connected to an end cap 310 by way of a non-stretchable link 313, e.g., made of polypropylene or other suitable material. When the user input mechanism 303 is activated by the user, e.g., as when the slide in FIG. 3A is moved in the direction shown by the arrow, the distal end 311 of the core member 304 is moved away from the ball end 312, releasing the embolic coil 308 as shown in FIG. 3C. The coil 308 is then detached from the distal end of the delivery member 307 and the core member 304.

Figure 4:
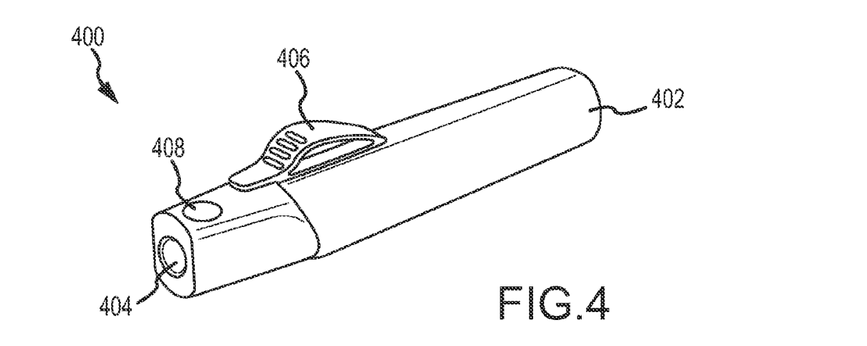
FIG. 4 illustrates an example of a coil detachment system with indicators, according to the present disclosure.

FIG. 4 illustrates an example of a coil detachment system 400 with indicators for use in placing an embolic coil structure, such as an embolic coil or stent, according to the present disclosure. Coil detachment system 400 includes a housing 402 with a feed cone 404 that is configured to receive an elongate delivery member, with a lumen, and an elongate core member (not shown), such as used to push an embolic coil to a desired location within the vasculature of a patient. The delivery member and core member each have a proximal end and a distal end, relative to the coil detachment system; for the treatment of an aneurysm in a patient, the distal ends of each would normally be presented to the vasculature of the patient. A user input mechanism 406, e.g., in the form of a user-activated slide switch, is present to move the proximal end of the core member with respect to the proximal end of the delivery member. Indicator 408 is present to indicate when the proximal end of the core member is properly seated within the housing 402 and/or when the coil (not shown) is detached from the core member, thus providing feedback to the user, such as a surgeon or other medical personnel.

Figure 5:
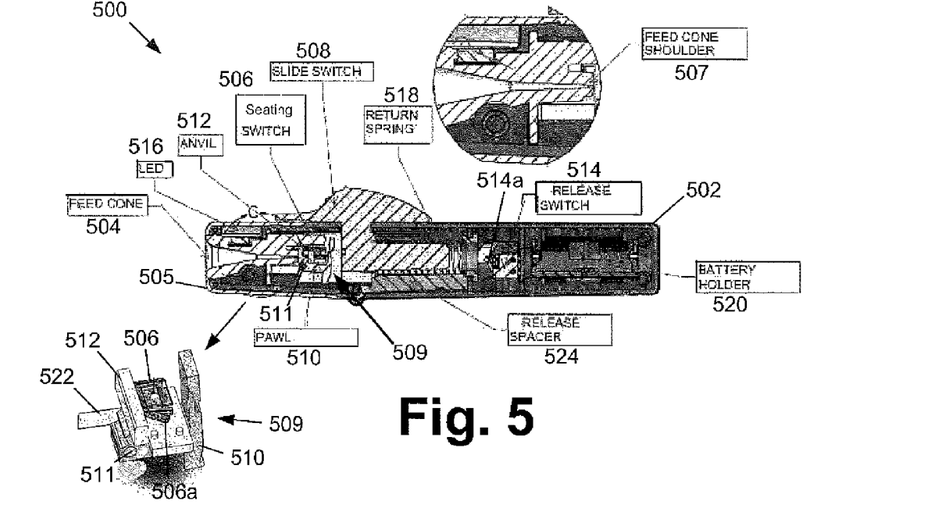
FIG. 5 illustrates a cross section view of a coil detachment system, according to the present disclosure.

FIG. 5 illustrates a cross section view of a coil detachment system 500 similar to system 400 of FIG. 4. Coil detachment system 500 includes a housing 502 with a feed cone 504 located in an end cap 505 of the housing 502. The feed cone 504 is configured to receive a delivery member and an elongate core member (not shown). The feed cone has a feed cone shoulder 507, which is configured to seat the delivery member and pass (by way of an aperture) a portion of the proximal end of the core member. The coil detachment system 500 includes a user-input mechanism 508 that receives an input signal from a user and relays the input signal to a grasping mechanism 509, e.g., a pawl 510 and anvil 512 assembly, within the housing 502. The pawl 510 can be configured to rotate about a pin 511, as shown. For seating of the proximal end of the core member, the grasping mechanism 509 receives the portion of the proximal end of the core member from the feed cone shoulder 507. The grasping mechanism 509 is configured to hold the proximal end of the core member for displacement of the proximal end of the core member relative to the proximal end of the delivery member when a user activates a user input mechanism 508, e.g., as described in further detail below for FIGS. 6A-6C. The displacement of the proximal end of the core member relative to the proximal end of the delivery member provides sufficient motion to effect detachment of a medical device, e.g., an embolic coil, at the distal ends of the core member and delivery member.

With continuing reference to FIG. 5, a first proximity sensor, e.g., a switch, 506 is present within system 500 to detect complete seating of the proximal end of the core member within the housing 502. Proximity sensor 506 can include a movable arm 506a as shown at the detailed enlargement of the grasping mechanism 509 shown at the lower left of the drawing. When the proximal end of the core member is fully seated, proximity sensor 506 can activate a first indicator 516, such as LED an assembly, which may for example emit light of a first color, blue in the embodiment shown in FIG. 5. Proximity sensor 506 may be connected to indicator 516 by a flexible circuit 522. In exemplary embodiments, first indicator 516 can include an LED assembly having multiple LEDs and/or filters, such that when activated each LED produces a different color of light output for a user. The first indicator 516 provides active feedback for the user to indicate complete seating of the core member within the housing 502 and that the core member is ready to be displaced for coil detachment.

A second proximity sensor 514, shown as a switch in FIG. 5, is present to indicate when the proximal end of the core member has traveled a predetermined distance relative to the seated proximal end of the delivery member, in response to the user-supplied input signal, e.g., movement of the slide 508 by the user, thus indicating detachment of the coil from the distal end of the core member. As shown, second proximity sensor 514 can include a movable arm 514a. The second proximity sensor 514 can activate a second indicator 516, also shown as LED assembly, which can emit light of a second color, e.g., green in this embodiment. The second color, e.g., green, confirms detachment of the embolic coil from the distal end of the core member. A release spacer 524 may be present to position the user input mechanism 508 a desired distance from the second proximity sensor 514.

In exemplary embodiments, a detection switch from Omron, as made commercially available by RS Components, e.g., as a single-pole single-throw normally-closed switch (SPST-NC) or a single-pole single-throw normally-open stock (SPST-NO) of leaf spring or hinged configuration, can be used for the first and/or second proximity sensors 506 and 514, for example. Such a switch is approximately 3.0×3.4× 0.9 mm (W×D×H) and can fit suitably within a coil detachment system as disclosed herein. For use as the first proximity sensor 506, such a switch may be configured to present the movable portion (moveable arm 506a) such that, when contacted by the proximal end of the core member, the switch 506 allows passage of the core member for adequate seating. Such a configuration is shown in the enlargement at the lower left of FIG. 5. Of course, while electromechanical switches may be used for the first and second proximity sensors 506 and 514, other types of proximity sensors may be used within the scope of the present disclosure. Examples, include but are not limited to, RF or capacitive proximity sensors, optical detectors, acoustic detectors, and the like. When optical detectors are utilized, any suitable optical wavelengths may be used (e.g., infrared, visible, and/or ultraviolet) and passive detectors (used without optical sources) and active detectors with corresponding sources in addition to detectors may be used. The detectors are selected with appropriate materials (e.g., semiconductor alloys) to detect the desired wavelength of optical radiation.

In exemplary embodiments, the grasping mechanism 509 includes a pawl 510 and anvil 512 assembly to hold the proximal end of the core member until being released by action of the user. In other embodiments, different types of grasping mechanism 509 may be used. For example, a pressure sensitive switch may be used to, receive the proximal end of the core member to activate a clamping force between a pair of blocks within the housing. The user's input signal, e.g., movement of the slide, may then displace the proximal end of the core member relative to the proximal end of the delivery member.

While LED assemblies with multiple LEDs each having a difference predominant peak wavelength (color) may be used as indicators, other types of indicators may be used. Examples include, but are not limited to, acoustic emitters such as speakers, and tactile/haptic indicators such as buttons or vibration generators, and the like. Further, for embodiments where optical indicators are used, light sources (e.g., such as white-light emitting LEDs), can be used with various filters to provide a desired color light. In exemplary embodiments, LUXEON® Rebel LEDs as made commercially available by the Philips Lumileds Lighting Company may be used with one or more suitable filters as light sources for an indicator.

Figure 6A:
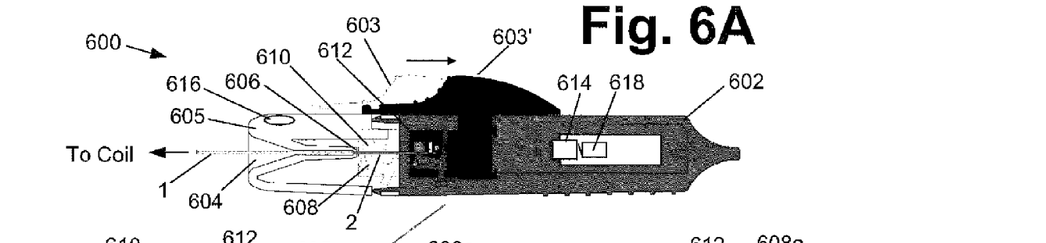
FIGS. 6A-6C illustrate operation of a thumb slide in conjunction with a pawl and anvil for an exemplary embodiment of a coil detachment system according to the present disclosure.
Figures 6B, 6C:
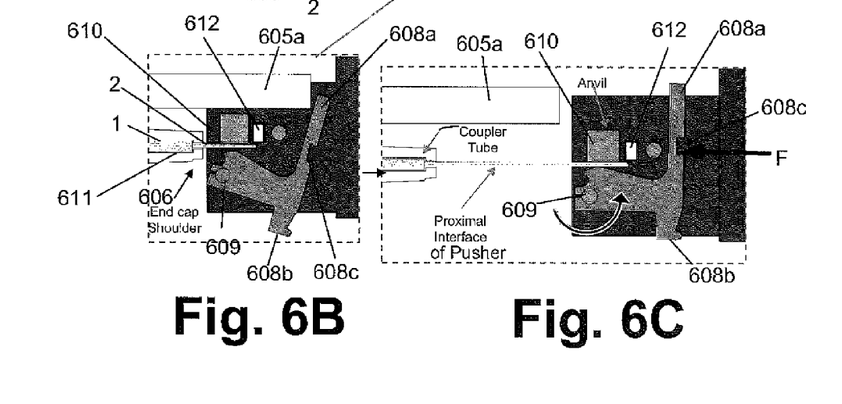

FIGS. 6A-6C depict an embodiment of a coil detachment system 600 with indicators, illustrating operation of a user input mechanism in the form of a thumb slide, in conjunction with a grasping mechanism in the form of a pawl and anvil, for coil detachment. Coil detachment system 600 includes a housing 602, a user input mechanism (e.g., slide 603), and a feed cone 604 configured within an end cap 605 to receive an elongate delivery member 1 with an elongate core member 2 such as used for placing an embolic coil structure within the vasculature of a patient. Housing 602 may be made of any suitable material. Examples include, but are not limited to, plastics, metals (e.g., 6000 series aluminum), or composites (such a carbon-fiber reinforced plastic).

The end cap 605 includes an end cap shoulder 606 configured at one end of the feed cone 604 to stop movement of the proximal end of the delivery member 1 while allowing further movement of the proximal end of the core member 1. Slide 603 can be part of a slide sub-assembly (e.g., 800 of FIG. 8), which may include a grasping mechanism, for example a pawl 608 and anvil 610, as well as a first proximity sensor 612, that all move within housing 602 in response to force applied to slide 603. The grasping mechanism, or pawl 608 and anvil 610 in the illustrated embodiments, can hold the proximal end of the core member 2 when slide 603 is moved, e.g., by a user such as a surgeon. The pawl 608 is rotatably mounted to the slide sub-assembly by pin 609. One or more indicators 616 are present to provide feedback to a user. First proximity sensor (e.g., a leaf spring electromechanical switch) 612 can detect the presence of core member 2 in a fully or sufficiently seated position within the housing 602. The slide sub-assembly includes a portion 614 that is configured to be brought into contact with a second proximity sensor or sensor 618, located within housing 602, when the slide 603 is moved to a position, shown by slide at 603', away from the feed cone 604. Housing 602 can include a suitable battery (not shown) for power used for the first and second proximity sensors 612, 618 and indicator(s) 616, in exemplary embodiments. The battery, first and second proximity sensors 612, 618, and indicator(s) 616 may be connected by a suitable flexible circuit (not shown). In alternative embodiments, when needed, electrical power may be supplied to system 600 by way of a power cord (not shown). In exemplary embodiments, slide 603 may be ergonomically shaped for a user's thumb or finger, as shown.

In operation, as slide 603 is moved by a user to a position away from the feed cone 604, shown by alternate position of slide at 603', a portion of the slide sub-assembly 614 is brought into contact with a second proximity sensor 618 within housing 602, as shown in FIG. 6A. Proximity sensor 618, in response, can cause activation of an indicator, e.g., a LED of a given color, as shown at 616.

With continued reference to FIGS. 6B-6C, operation of the pawl 608 and anvil 610 is further explained. When slide 603 and the related slide sub-assembly are in a position proximal to the feed cone 604, a portion of end cap 605a (or suitable portion of housing 602) contacts pawl 608 at portion 608a, causing the pawl 608 to rotate (or be at an angular displacement) about pin 609, such that end portions 608a and 608b are in a configuration similar to the one shown in FIG. 6B. Such a configuration of the pawl 608 relative to anvil 610 allows movement of the core member 2 along an axis parallel to the delivery member and through an orifice 611 in the end cap shoulder 606. While not shown in the drawings, a spring may be present to supply a bias force (shown as F) to the pawl 608 at spring coupling portion 608c.

When a user moves the slide 603, e.g., after indication that an elongate core member is fully seated in the coil detachment system 600, to a position away from feed cone 604 such as shown in FIG. 6C, the bias force F on pawl 608 causes the pawl to rotate about pin 609 to a position similar to that shown in FIG. 6C. In such a position, a contact surface 608d of the pawl 608 securely holds the core member 2 against the anvil 610 as the slide sub-assembly is moved. In this way, the proximal end of the core member 2 is drawn proximally with the slide sub-assembly. As the end cap shoulder 606 at the proximal end of the feed cone 604 stops proximal movement of the delivery member 1, the delivery member 1 is not drawn proximally with the core member 2, and the core member 2 is thus displaced or moved relative to the proximal end of the delivery member 1. As a result, the distal end of the core member 2 is displaced an equal distance along the axis of the delivery member 1 (see FIGS. 3A-3C). The distance of travel of the slide 603 and slide sub-assembly can be designed and manufactured to match or correspond to a distance that sufficiently ensures detachment of a coil from an elongate core member 2. This movement of the distal end of the core member 2 can detach an embolic coil, or other medical device, from the distal end of the core member. This travel distance of the core member, and slide sub-assembly, can be derived empirically from analysis of a number of embolic coils and pusher systems to determine a distance that virtually guarantees that detachment has occurred, e.g., to an acceptable desired statistical error rate such as three-sigma, six-sigma, etc.

Figure 7:
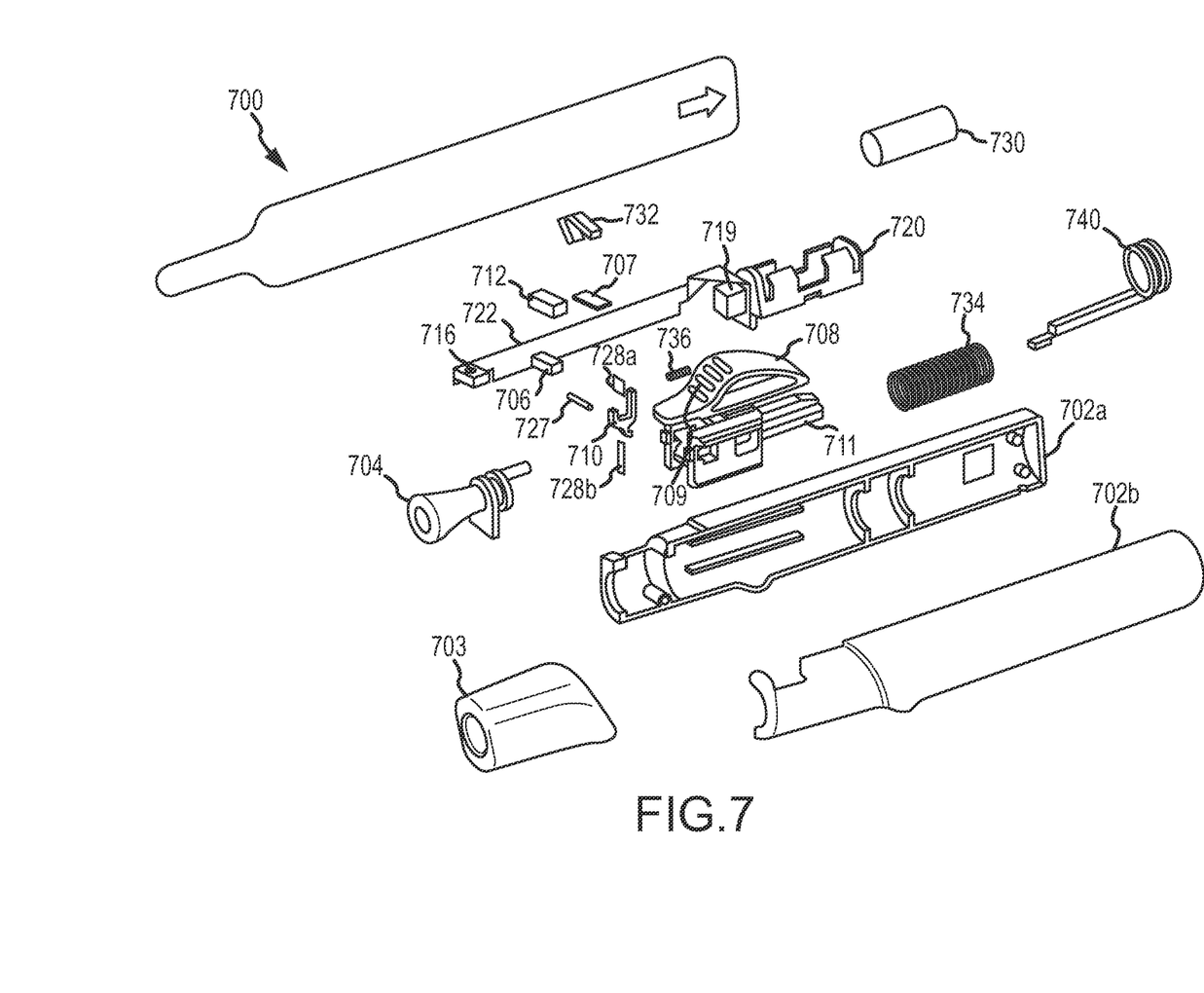
FIG. 7 depicts a perspective exploded view of an exemplary embodiment of a coil detachment system with indicators, according to the present disclosure.

FIG. 7 depicts a perspective exploded view of an exemplary embodiment of an coil detachment system 700 including indicators 716, according to the present disclosure. Coil detachment system includes a housing arranged in two mating halves 702a and 702b and an end cap 703. A feed cone 704 is configured to receive an elongate delivery member and an elongate core member, such as used for the placement of embolic coil structures (e.g., coils and/or stents). The system 700 includes a user input mechanism in the form of a slide sub-assembly 708 that includes a surface 709 adapted for contact with a user and an extension portion 711 that is adapted to contact a proximity sensor 719 to indicate detachment of an embolic coil (not shown), similar to as explained for FIGS. 3A-3C. A grasping mechanism is present which includes a pawl 710 and anvil 712, with the pawl 710 being rotatably attached to slide sub-assembly 708 by a pin 727. The anvil 712 is also mounted to slide sub-assembly 708. A proximity sensor 706 is included to detect when an elongate core member is seated correctly within the system 700. A spacer 707 and tab 732 facilitate placement of the anvil 710 and can provide a stop surface for preventing travel of an elongate core member beyond a desired location within system 700. Spring 736 can provide a bias force between pawl 710 and slide sub-assembly 708. Strips or coatings 728a-728b of suitable materials such as polytretafluoroethylene (PTFE), Teflon®, or a suitable polymeric coating, or the like, can optionally be placed on the pawl 710 at a location or locations susceptible to contact with the end cap 703 and/or housing 702a-702b.

Continuing with the description of system 700, flexible circuit 722 provides a connection between proximity sensors 706 and 719, as well as indicators 716 and a battery holder 720, which is configured to receive a suitable battery 730. A release spacer 740 can control the starting position of the slide sub-assembly 709, as biased by bias spring 734, within the housing of the system 700.

Figure 8:
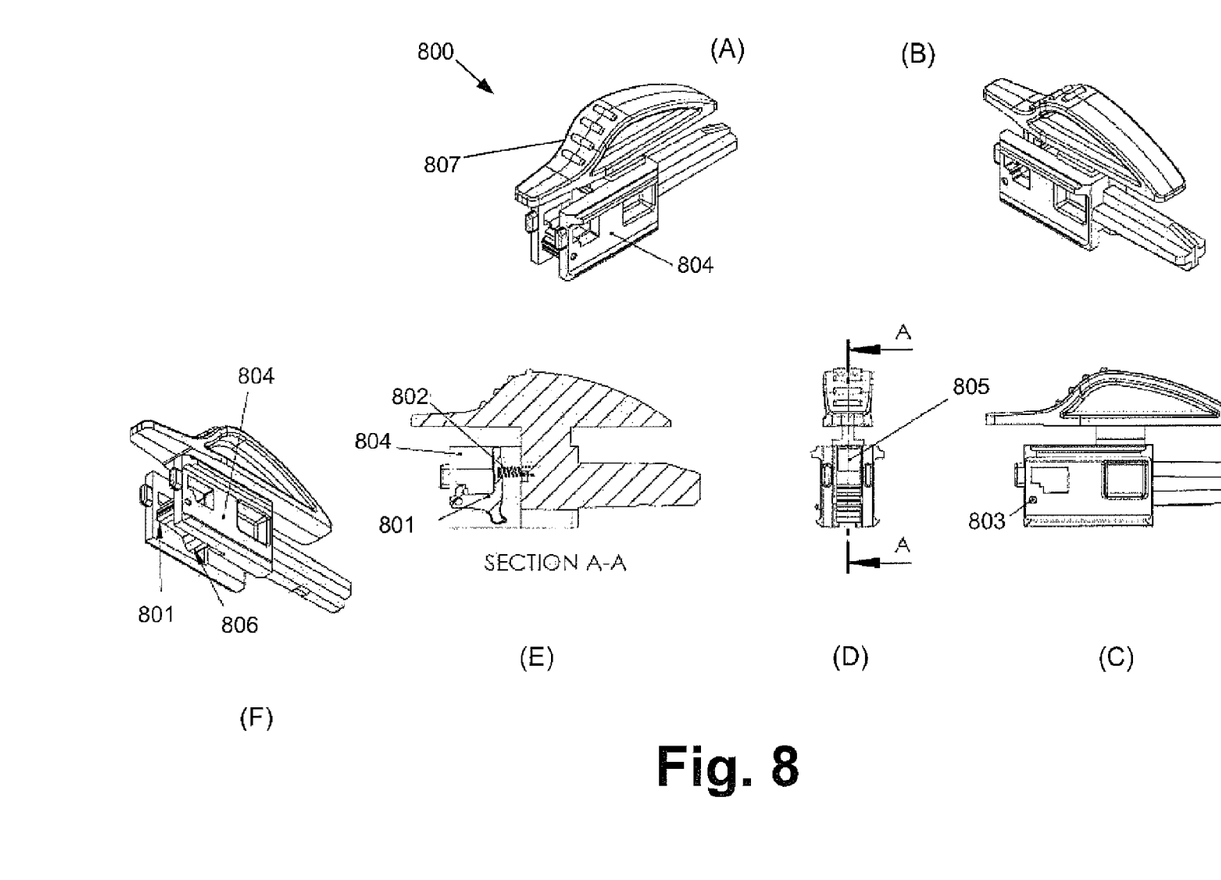
FIG. 8 includes views (A)-(F) illustrating an example of a user input mechanism in the form of a slide switch subassembly according to the present disclosure.

FIG. 8 includes views (A)-(F) illustrating an example of a slide switch sub-assembly 800 that functions as a user input mechanism according to the present disclosure. Slide switch sub-assembly 800 includes a pawl 801 and pawl spring 802, which may both be used as part of a grasping mechanism, in conjunction with an anvil (not shown). Pawl 801 is configured to rotate about dowel pin 803. Optional PTFE coatings 805 and 806 are also shown. A contact surface 807 is present on the slide body 804 of the sub-assembly 800 and is configured for contact with a user, e.g., a surface with knurled features for contacting a user's thumb. The main body 804 of the sub-assembly is shown in relation to an extension 808 that is configured to contact a proximity sensor, e.g., proximity sensor 618 as depicted in FIG. 6.

Figure 9:
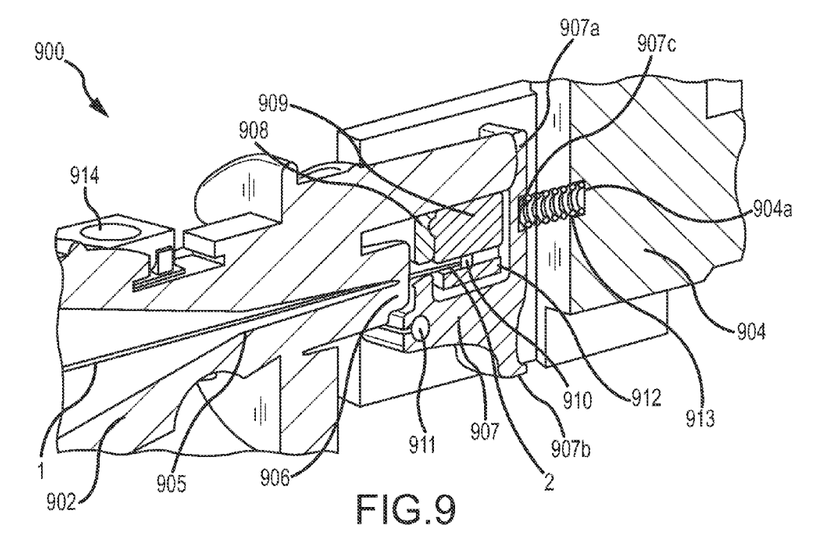
FIG. 9 depicts a perspective view of a grasping mechanism in the form of a pawl and anvil with micro switch for a coil detachment system, according to the present disclosure.

FIG. 9 depicts a perspective view of a portion of a coil detachment system 900 featuring a pawl and anvil with a micro switch proximity sensor according to an exemplary embodiment. System 900 includes an end cap 902 and a slide sub-assembly 904. End cap 902 can fit or mate with a housing (not shown) that is adapted to be hand-held. End cap 902 includes a feed cone 905 that is configured to receive an elongate delivery member 1 and elongate core member 2, such as used to place an embolic coil structure in a patient's vasculature, e.g., for treatment of an aneurysm. A pawl 907 and anvil 908 are configured within the slide sub-assembly 904. A proximity sensor, e.g., leaf spring microswitch, 912 is present to detect adequate seating of a core member within the system 900. Spacer 909 can facilitate mounting of the anvil 908 and/or proximity sensor 912.

Continuing with the description of system 900, the pawl is rotatably mounted to the slide sub-assembly 904 by pin 911. The pawl 907 includes extensions 907a and 907b that can facilitate positioning of the pawl 907 during operation of the system 900. To bias the pawl 907 in the position shown, a bias spring 913 is connected to the slide sub-assembly at location 904a and at the pawl at location 907c. The end cap 902 also includes a shoulder 906 with an aperture (not shown) that can hold the proximal end of the delivery member 1 and allow the inner core member 2 to pass through the aperture to extend to a stop 910, and thus be fully or adequately seated within the system between the pawl 907 and anvil 908.

Figure 10:
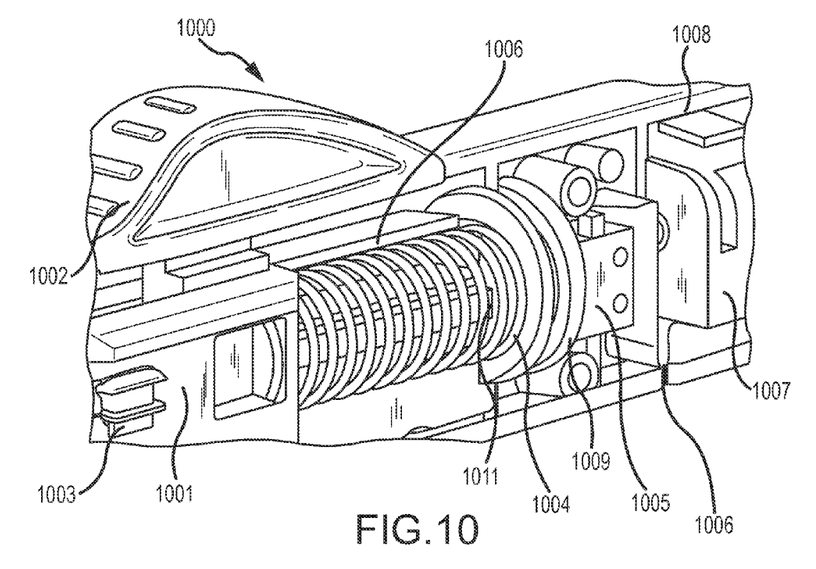
FIG. 10 depicts a perspective view of a slide and release micro switch of a coil detachment system, in accordance with the present disclosure.

FIG. 10 depicts a perspective view of a portion of a coil detachment system 1000 featuring a user input mechanism in the form of a slide sub-assembly, and a release micro switch, in accordance with the present disclosure. As shown, system 1000 includes a slide sub-assembly main body 1001 and textured surface 1002 for contact by a user. The sub-assembly main body 1001 holds a first proximity sensor 1003 that is functional to detect adequate seating of an elongate core member (not shown) within the system 1000.

With continued reference to FIG. 10, a release spacer 1009 can position the sub-assembly at an initial desired position within a housing 1008. A bias spring 1004 can provide bias force to the sub-assembly 1001, as shown. A second proximity sensor 1005 can detect when an extension 1011 of the sub-assembly 1001 comes into proximity of, e.g., contact with, the proximity sensor 1005. A flexible circuit 1006 connects the proximity sensors to a power source, indicated by battery holder 1007, as well as one or more indicators (not shown), that provide active feedback to alert the user when an elongate core member is fully seated within the system 1000 and when the proximal end of the core member has been displaced a certain distance relative to the proximal end of the related delivery member, indicating detachment of an embolic coil structure.

Accordingly, embodiments of the present disclosure can advantageously provide coil detachment systems for pushing an embolic coil structures to a desired location in a patient's vasculature by use of a pusher catheter having an elongate core member, includes a housing with feedback indicators such as colored light emitting diodes to indicate proper seating of the core member within housing and the and detachment of the coil from the core member.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

In reading the present disclosure, one skilled in the art will appreciate that embodiments of the present disclosure, or portions thereof, can be implemented in or with hardware, software, firmware, or any combinations of such, and by use of one or more communication networks. Suitable software can include computer-readable or machine-readable instructions for performing methods and techniques (and portions thereof) of designing and/or controlling the implementation of data acquisition and/or data manipulation. Any suitable software language (machine-dependent or machine-independent) may be utilized. Moreover, embodiments of the present disclosure can be included in or carried by various signals, e.g., as transmitted over a wireless RF or IR communications link or downloaded from the Internet.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

What is claimed is:

1. A medical device detachment system for placement of a medical implant in a patient's vasculature, the system comprising:
    a housing configured to receive a proximal end of an elongate delivery member and a proximal end of an elongate core member slidably disposed within the delivery member;
    a grasping mechanism disposed within the housing and configured to grasp a portion of the core member in response to receiving an input signal;
    a user input mechanism configured to receive the input signal and permit movement of the grasping mechanism to grasp the proximal end of the core member;
    a first sensor configured to provide an output signal confirming placement of the proximal end of the core member at a determined position within the housing;
    a second sensor configured to provide an output signal indicative of a proximity of the grasping mechanism relative to the delivery member; and
    an indicator connected to the first and second sensors and configured to receive one or more output signals from the first and second sensors and to provide corresponding indication signals to a user when one or more output signals are received from the first or second sensors.

2. The system of claim 1, wherein the grasping mechanism is moveable from a first position within the housing to a second position within the housing, and wherein the second sensor is configured to detect when the grasping mechanism is at the second position.

3. The system of claim 1, wherein the grasping mechanism comprises a pawl and anvil.

4. The system of claim 1, wherein the user input mechanism comprises a slide.

5. The system of claim 1, wherein the indicator comprises a light emitting diode (LED).

6. The system of claim 5, wherein the LED comprises a plurality of LEDs.

7. The system of claim 5, wherein the indicator comprises two optical filters, each configured to pass a different wavelength band.

8. The system of claim 1, wherein the first sensor comprises a microswitch.

9. The system of claim 8, wherein the microswitch comprises a leaf-spring microswitch.

10. The system of claim 1, wherein the second sensor comprises a microswitch.

11. The system of claim 10, wherein the microswitch comprises a hinge microswitch.

12. The system of claim 1, wherein the first sensor comprises a capacitive sensor.

13. The system of claim 1, wherein the second sensor comprises a capacitive sensor.

14. The system of claim 1, wherein the first sensor comprises a RF sensor.

15. The system of claim 1, wherein the second sensor comprises a RF sensor.

16. The system of claim 1, wherein the first sensor comprises an acoustic sensor.

17. The system of claim 1, wherein the second sensor comprises an acoustic sensor.

18. The system of claim 1, wherein the first sensor comprises an optical detector.

19. The system of claim 1, wherein the second sensor comprises an optical detector.

20. The system of claim 1, wherein the indicator comprises a speaker.

21. The system of claim 1, wherein the indicator comprises a vibration generator.

22. The system of claim 1, wherein the indicator comprises a button disposed on the surface of the housing.

23. The system of claim 1, further comprising a delivery member having a proximal end and a distal end, and an elongate core member disposed within the delivery member and having a proximal end and a distal end.

24. The system of claim 23, further comprising an embolic coil structure releasably attached to the distal end of the core member.

\* \* \* \* \*